(12) United States Patent
Miyahara et al.

(10) Patent No.: US 7,695,907 B2
(45) Date of Patent: Apr. 13, 2010

(54) GENE DETECTION FIELD-EFFECT DEVICE AND METHOD OF ANALYZING GENE POLYMORPHISM THEREWITH

(75) Inventors: Yuji Miyahara, Ibaraki (JP); Toshiya Sakata, Ibaraki (JP)

(73) Assignee: National Institute for Materials Science, Ibaraki (JP)

( * ) Notice: Subject to any disclaimer, the term of this patent is extended or adjusted under 35 U.S.C. 154(b) by 678 days.

(21) Appl. No.: 10/587,941

(22) PCT Filed: Feb. 3, 2005

(86) PCT No.: PCT/JP2005/001987

§ 371 (c)(1), (2), (4) Date: Oct. 20, 2006

(87) PCT Pub. No.: WO2005/075638

PCT Pub. Date: Aug. 18, 2005

(65) Prior Publication Data

US 2008/0286762 A1    Nov. 20, 2008

(30) Foreign Application Priority Data

Feb. 3, 2004   (JP) .............................. 2004-026821

(51) Int. Cl.
*C12Q 1/68* (2006.01)
(52) U.S. Cl. ........................................................ 435/6
(58) Field of Classification Search .................. None
See application file for complete search history.

(56) References Cited

U.S. PATENT DOCUMENTS 6,475,728 B1 * 11/2002 Martin et al. .................. 435/6

2003/0148301 A1   8/2003   Aono et al.
2003/0186262 A1 * 10/2003   Cailloux ........................ 435/6

FOREIGN PATENT DOCUMENTS

JP          2002-272463        9/2002
WO          01-42498           6/2001

OTHER PUBLICATIONS

Y. Miyahara et al., "Potentiometric Detection of DNA Molecules Using Field Effect Transistor", The Japan Society of Applied Physics., No. 3, p. 1180, 30a-S-2, 2003 (English translation enclosed).
Y. Miyahara et al., "Biochip Using Micromachining Technology", Journal of Institute of Electrostatics Japan, vol. 27, No. 6, pp. 268-272, 2003 (English translation enclosed).
T. Sakata et al.,Detection of DNA Hybridization by Genetic Transistor, The Japan Society of Applied Physics, No. 3, p. 1179, 30a-S-1, 2003 (English translation enclosed).
T. Sakata et al., Potentiometric Detection of DNA Molecules Using Genetic Field Effect Transistor, Denki Gakkai Kenkyukai Shiryo Chemical Sensor Kenkyukai, pp. 1-5, CH5-03-51-55, 2003 (English translation enclosed).

* cited by examiner

*Primary Examiner*—Christopher M. Babic
(74) *Attorney, Agent, or Firm*—Wenderoth, Lind & Ponack, L.L.P.

(57)  ABSTRACT

A gene detection field-effect device provided with an insulation film (2), a semiconductor substrate (3), and a reference electrode (4), includes: (a) the insulation film (2) including a nucleic acid probe (5) immobilized on one of the surfaces thereof and is in contact with a sample solution (6) containing at least one type of a target gene (601) for detection and analysis; (b) the semiconductor substrate (3) being installed so as to abut against the other surface of the insulation film (2); and (c) the reference electrode (4) being provided in the sample solution (6).

7 Claims, 13 Drawing Sheets

SEQUENCE LISTING

<160> NUMBER OF SEQ ID NOS: 4

<210> SEQ ID NO 1
<211> LENGTH: 11
<212> TYPE: DNA
<213> ORGANISM: Artificial
<220> FEATURE:
<223> OTHER INFORMATION: Synthetic Construct

<400> SEQUENCE: 1
cgtcctctga a                                                         11

<210> SEQ ID NO 2
<211> LENGTH: 11
<212> TYPE: DNA
<213> ORGANISM: Artificial
<220> FEATURE:
<223> OTHER INFORMATION: Synthetic Construct

<400> SEQUENCE: 2
cgtcctctga g                                                         11

<210> SEQ ID NO 3
<211> LENGTH: 9
<212> TYPE: DNA
<213> ORGANISM: Artificial
<220> FEATURE:
<223> OTHER INFORMATION: Synthetic Construct

<400> SEQUENCE: 3 catacacta                                                             9

<210> SEQ ID NO 4
<211> LENGTH: 9
<212> TYPE: DNA
<213> ORGANISM: Artificial
<220> FEATURE:
<223> OTHER INFORMATION: Synthetic Construct

<400> SEQUENCE: 4 catacactg                                                             9

GENE DETECTION FIELD-EFFECT DEVICE AND METHOD OF ANALYZING GENE POLYMORPHISM THEREWITH

This application is a U.S. national stage of International Application No. PCT/JP2005/001987 filed Feb. 3, 2005.

TECHNICAL FIELD

The invention in this application relates to a gene detection field-effect device and a method of analyzing gene polymorphism therewith. More specifically, the invention in this application relates to a novel gene detection field-effect device and a method of analyzing gene polymorphism therewith which enables detection and analysis of genes with high degree of sensitivity and high degree of accuracy, and reduction of the size and cost of a gene polymorphism analyzing system in comparison with the related art.

BACKGROUND ART

Under the circumstance such that decoding of the whole base sequence of human genome is terminated and decoding of base sequence for genome of other living organisms is in breakthrough, a huge amount of base sequence information is being accumulated. It seems that a gene-related technology will be dramatically developed in a wide range of fields such as diagnosis of various diseases, development of medicaments, breed improvement of agricultural products by revealing the function of gene in the living organisms on the basis of the genome base sequence information. A base of such development of the new field is information on gene expression and function in addition to the base sequence information. DNA chip or DNA microarray (hereinafter referred to as "DNA microarray" as a generic nomination of both) has been developed as a technology for performing a large scale decoding of the gene function and the gene expression and leading the same to the genetic screening. However, many of the DNA microarrays in the status quo are based on a principle of fluorescence detection. It has problems that laser or complex optical system is required, and the system is upsized and expensive.

Most of the currently developed DNA microarrays are based on a principle of detection of double strand DNA on the basis of hybridization and selectivity of reactions is not very high. Therefore, there is a problem in accuracy of the gene polymorphism analysis. In particular, in the field of medical practice, it is necessary to detect gene polymorphism or Single Nucleotide Polymorphism (hereinafter, it may be abbreviated as SNP) simply in high degree of accuracy for realization of a tailor-made medical practice. Therefore, a technology which can satisfy increase of both simplicity and accuracy has been required.

As a method of resolving these problems, some DNA microarrays of a current detection system which is combined with an oxidation-reduction indicator are reported. For example, there is developed a system for detecting a target gene by fixing an end of a molecule denominated as molecule wire to a metal electrode, hybridizing a nucleic acid probe to the other end thereof, and the detecting oxidation-reduction indicator and giving receiving of electrons of metal electrode as variations in electric current on the basis of hybridization with respect to the target gene (Non-Patent Document 1 and Non-Patent Document 2).

There is also developed a system for detecting hybridization by measuring the oxidation-reduction current at the metal electrode using Ferrocenylnaphthalene Diimide as an electrochemically active indicator (Non-Patent Document 3).

There is further developed a medicinal virtue inspection system for hepatitis C using a current detection system DNA tip (Non-Patent Document 4). In this system, an expensive laser, a complex optical system or the like are not necessary, a simple and compact system can be established.

However, in the case of the four systems in Non-Patent Documents 1 to 4, since detection is based on the oxidation-reduction reaction on the metal electrode in principle, there is a problem such that if there exists an oxidizing substance or a reducing substance in a sample (for example, ascorbic acid), an electric current based on oxidation or reduction flows, which hinders detection of gene and results in deterioration of detection accuracy. In association with measurement of the electric current, electrode reaction is proceeded on the metal electrode. Since the electrode reaction is irreversible and non-equilibrium reaction, corrosion of the electrode or generation of gas may be resulted, and consequently, separation of immobilized nucleic acid or impairment of stability of current measurement may be resulted. Therefore, there is a problem such that the detection accuracy may be deteriorated specifically when measurement is repeatedly performed.

There is also reported a trial to detect the hybridization of DNA using the field-effect device (Non-Patent Document 5). This technology is for detecting a change in electric charge by hybridization using the field effect on the basis of the fact that the DNA molecule has a negative electric charge in solution. However, since the DNA probe formed on a substrate has the negative electric charge by nature, the amount of change in electric charge by the hybridization of the target gene is small, and hence identification from non-specific adsorption is impossible. Therefore, increase in sensitivity and improvement of accuracy have been subjects to be solved for genetic screening. It is also difficult to detect a slight difference (one base is different) between two genes such as the Single Nucleotide Polymorphism (SNP) since both the sensitivity and accuracy (selectivity) are low.

Non-Patent Document 1: Nature Biotechnology, vol. 16, p. 27-31, 1998

Non-Patent Document 2: Nature Biotechnology, vol. 16, p. 40-44, 1998

Non-Patent Document 3: Anal, Chem, 72, p. 1334-1341, 2000

Non-Patent Document 4: Intervirology, 43, p. 124-127, 2000

Non-Patent Document 5: J. Phys. Chem. B., 101 p2980-2985, 1997

DISCLOSURE OF INVENTION

In view of such circumstances, it is an object of the invention in this application to provide a novel gene detection field-effect device and a method of analyzing gene polymorphism therewith that enables detection and analysis of genes with high degree of sensitivity and high degree of accuracy, and reduction of the size and cost of the gene polymorphism analyzing system in comparison with the related art.

The invention in this application provides the aspects of the invention from (1) to (9) shown below as means for achieving the above-described object.

(1) A gene detection field-effect device provided with an insulation film, a semiconductor substrate, and a reference electrode, including:

(a) the insulation film including a nucleic acid probe immobilized on one of the surfaces thereof and is in contact with sample solution containing at least one type of target gene;

(b) the semiconductor substrate being installed so as to abut against the other surface of the insulation film; and (c) the reference electrode being provided in the sample solution;

(2) A gene detection field-effect device wherein two of the gene detection field-effect devices described in (1) are provided and at least two types of nucleic acid probes including a wild-type (normal-type) nucleic acid probe having a base sequence which is complementary with a base sequence of a target gene and a mutant-type nucleic acid probe having a base sequence which is non-complementary with the base sequence of the target gene are immobilized to the respective insulation films of the gene detection field-effect devices;

(3) The gene detection field-effect device according to (2), wherein a base at a non-immobilized end, which is an end of the nucleic acid probe not immobilized to the insulation film of the mutant-type nucleic acid probe is different from a base at a non-immobilized end of the wild-type nucleic acid probe;

(4) The gene detection field-effect device according to any one of (1) to (3), wherein at least one type of the nucleic acid probe is selected from a group of oligonucleotide, a complementary DNA (cDNA) and peptide nucleic acid (PNA);

(5) The gene detection field-effect device according to any one of (1) to (4), wherein the nucleic acid probe is immobilized via a metal electrode;

(6) The gene detection field-effect device according to (5), wherein at least one type of the metal electrode is selected from a group of white gold, gold, silver, palladium, titan, and chrome;

(7) The gene detection field-effect device according to any one of (1) to (6), wherein a heater and a temperature sensor are further integrated;

(8) A method of analyzing gene polymorphism using a gene detection field-effect device according to any one of (1) to (7), including the steps of;

(a) bringing a nucleic acid probe immobilized to an insulation film into contact with sample solution containing at least a target gene to hybridize the nucleic acid probe and the target gene on the insulation film;

(b) introducing cleaning liquid on the insulation film to remove the target gene which is not reacted;

(c) introducing deoxyadenosine triphosphoric acid (dATP), deoxyguanosine triphosphate (dGTP), deoxycytidine triphosphate (dCTP), and deoxythymidine triphosphate (dTTP) as ground substances onto the insulation film along with Taq DNA polymerase as an enzyme for elongation to cause elongation;

(d) introducing cleaning liquid on the insulation film to remove the enzyme and the ground substances which are not reacted; and (e) introducing buffer liquid on the insulation film and measuring an output value of the gene detection field-effect device; and (9) The method of analyzing gene polymorphism according to (8), wherein measuring the output value in step (e) includes measuring a differential output value V1 between a first gene detection field-effect device in which the wild-type nucleic acid probe is immobilized and a third gene detection field-effect device in which the nucleic acid probe is not immobilized on the insulation film; measuring a differential output value V2 between a second gene detection field-effect device in which the mutant-type nucleic acid probe is immobilized and the third gene detection field-effect device, and classifying into three patterns; a pattern in which V1 is larger than V2 (V1>V2), a pattern in which V1 and V2 is almost the same (V1≈V2), and a pattern in which V1 is smaller than V2 (V1<V2) and displaying the same.

Figure 1:
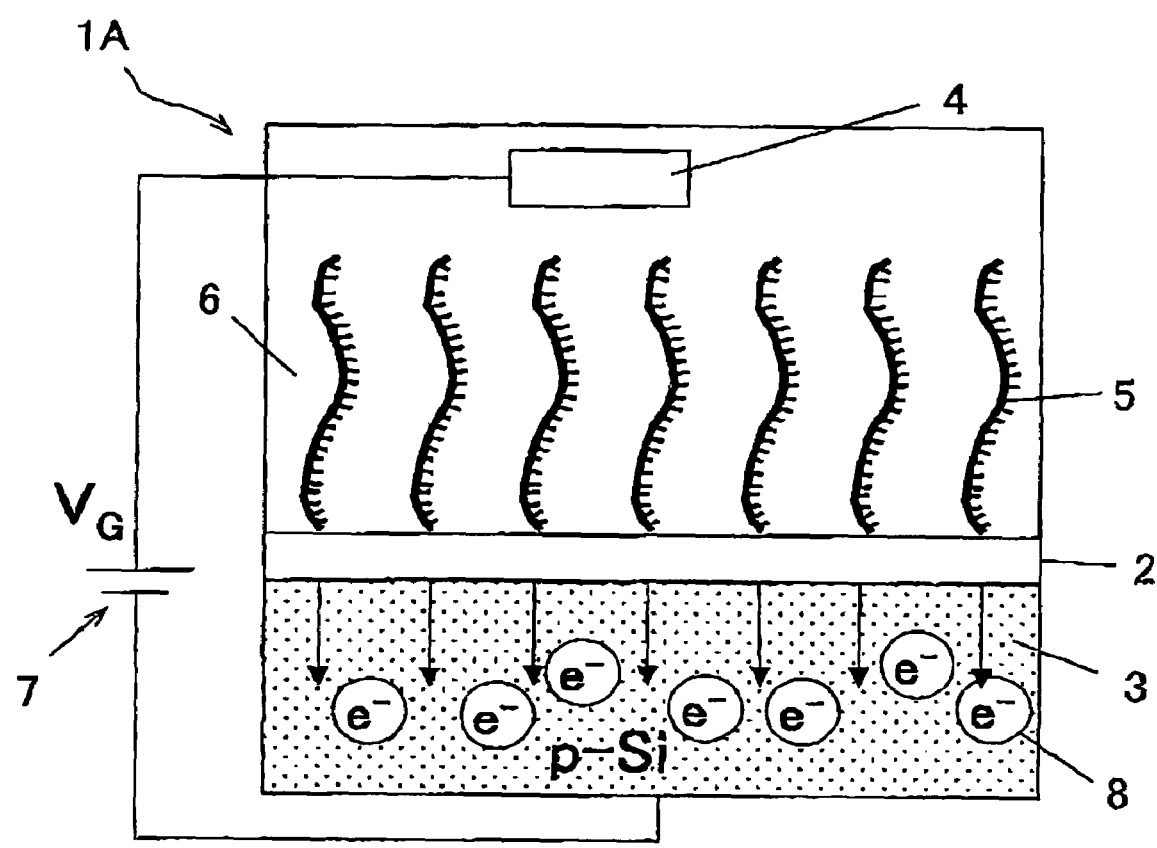
FIG. 1 is a cross-sectional pattern diagram illustrating an embodiment of a gene detection field-effect device according to the invention in this application.

Reference numerals in the drawings designate members shown below.
1A gene detection field-effect device
1B, 1B' gene detection field-effect transistor
1C gene detection field-effect transistor array
2 insulation film
201 gate insulation film area
3 semiconductor substrate
4 reference electrode
5 nucleic acid probe
501 wild-type nucleic acid probe
502 mutant-type nucleic acid probe
503 immobilized end
504 non-immobilized end
6 sample solution
601 target gene
7 gate electrode
8 electron
9 source n-type area
10 drain n-type area
11 drain electrode
12 drain ampere meter
13 metal electrode
14 intercalator
15 heater
16 temperature sensor
17 p-well
18 silicon substrate
19 insulation film
20 heat-conductive substance
21 opening
22 copper plate
23 Pertier element
24 flow cell
25 flow channel
26 sample
27 reagent
28 buffer liquid
29 cleaning liquid
30 valve
31 pump
32 dispenser
33 waste liquid bottle
34 reference electrode
35 3M KCl solution
36 liquid-liquid coupling
37 signal processing circuit
38 printed board
39 wire
40 pin
41 protection cap

BEST MODE FOR CARRYING OUT THE INVENTION

The invention in this application has the characteristics shown above, and embodiments thereof will be described in detail below.

A characteristic of the invention in this application is a capability of detecting and analyzing a difference of one base between two genes, that is, detecting and analyzing gene polymorphism or Single Nucleotide Polymorphism (SNP) with high degree of sensitivity and high degree of accuracy by combining a gene detection field-effect device according to the invention in this application and a molecular biological reaction. Referring now to FIG. 1 to FIG. 13, the gene detection field-effect device and a method of SNP analysis with high-accuracy therewith according to the invention in this application will be described below.

FIG. 1 is a cross-sectional pattern diagram illustrating an embodiment of a gene detection field-effect device according to the invention in this application.

As shown in FIG. 1, a gene detection field-effect device (1A) according to the invention in this application at least includes an insulation film (2), a semiconductor substrate (3), and a reference electrode (4).

A nucleic acid probe (5) is immobilized on one of surfaces of the insulation film (2), and is kept in contact with a sample solution (6) which at least contains the target gene. The nucleic acid probe (5) has a base sequence which is complementary with a base sequence of the target gene which can be hybridized with the target gene (described later) which is an object of detection and analysis. The insulation film (2) has a structure characterized by provision of the semiconductor substrate (3) on the other surface thereof. The material of the semiconductor substrate (3) is not specifically limited as long as it has a function thereof, and may be p-Si4 (silicon) or germanium, or the like.

The gene detection field-effect device (1A) according to the invention in this application is provided with the reference electrode (4) in the sample solution (6), which is electrically connected to the semiconductor substrate (3). It is also possible to provide a gate electrode (7) and apply a voltage $V_G$ thereto as needed.

The mode, length and the like of the nucleic acid probe (5) are not specifically limited as long as it can be hybridized with the target gene as an object of detection and analysis and can be detected and analyzed. For example, natural oligonucleotide, artificial oligonucleotide, cDNA fragment, peptide nucleic acid, and the like are preferable. The length is preferably composed of 300 or less bases in general, and in particular, when the natural or artificial oligonucleotide is used, it is more preferable to use the nucleic acid fragment including 80 or less bases.

The insulation film (2) may be formed of a material such as silicon dioxide ($SiO_2$), silicon nitride (SiN or $Si_3N_4$), aluminum oxide ($Al_2O_3$), tantalum oxide ($Ta_2O_5$) independently or in combination. In general, it is preferable to employ a two-layer structure formed by laminating silicon nitride (SiN), aluminum oxide ($Al_2O_3$), tantalum oxide ($Ta_2O_5$) or the like on silicone oxide ($SiO_2$) in order to maintain the electrical characteristic of a surface of the semiconductor substrate (3).

In order to immobilize the nucleic acid probe (5) on the surface of the insulation film (2), an end of the nucleic acid probe (5) is chemically modified with amino group ($NH_2$ group), thiol group (SH group), biotin or the like first. For example, when the nucleic acid probe (5) which is chemically modified with the amino group is employed, the surface of the insulation film (2) is chemically modified with animopropylethoxysilane, polylysine or the like to introduce amino group on the surface of the insulation film (2) for causing the same to produce a response with glutaraldehyde or phenylene di-isocyanate (PDC), whereby the nucleic acid probe (5) which is chemically modified with amino group is immobilized on the surface of the insulation film (2).

When immobilizing the nucleic acid probe (5) chemically modified with thiol group on the surface of the insulation film (2), it is also possible to form a thin gold film on the insulation film (2) and immobilize the nucleic acid probe (5) utilizing hydrophilic property between the thiol group and gold. When immobilizing the nucleic acid probe (5) chemically modified with biotin, the nucleic acid probe (5) is immobilized on the surface of the insulation film (2) by introducing streptavidin on the surface of the insulation film (2) and utilizing the hydrophilic property between the biotin and streptavidin.

When the nucleic acid probe (5) is actually immobilized, solution containing the nucleic acid probe (5) is dropped or spotted only on the surface of the insulation film (2) to cause the same to produce a chemical response with the function group on the insulation film (2) to immobilize the nucleic acid probe (5). The nucleic acid probe (5) may be immobilized via the metal electrode. The metal electrode may be, for example, white gold, gold, silver, palladium, titan, chrome, and so on.

The sample solution (6) contains a number of genes including the target gene as an object of detection and analysis. As described above, since the nucleic acid probe (5) having the base sequence complementary with the base sequence of the target gene is immobilized on the insulation film (2) of the gene detection field-effect device (1A), the target gene and the nucleic acid probe (5) are hybridized under an adequate reaction condition to form a double strand.

In addition, only the double strand sample formed by hybridizing the target gene and the nucleic acid probe (5) can be efficiently elongated by introducing reagents for achieving elongation of the gene (Taq polymerase, dATP, dGTP, dCTP, dTTP, and so on) into the sample solution (6) and applying temperature control such as heating operation and/or cooling operation to the gene detection field-effect device (1A). In other words, since the gene which is not the target gene contained in the sample solution (6) and the immobilized nucleic acid probe (5) cannot form the double strand by hybridization, elongation is not accelerated as a matter of course.

Figure 9:
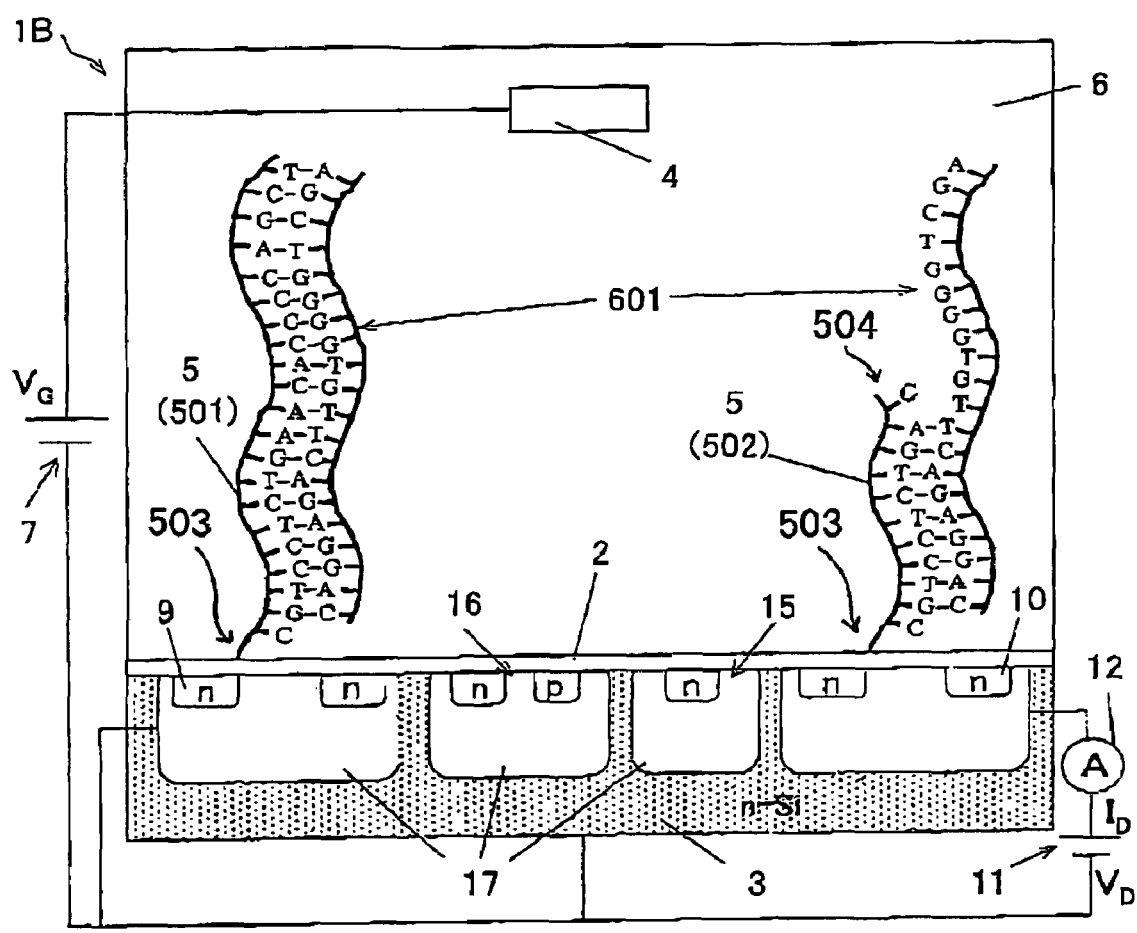
FIG. 9 is a cross-sectional pattern diagram showing a state in which a heater and a temperature sensor is integrated in the gene detection field-effect transistor composed of the gene detection field-effect device composed of the gene detection field-effect device according to the invention in this application.

Temperature control means in the gene detection field-effect device (1A) can control the reaction temperature for hybridization and elongation to an optimal value by integrating a heater (15) and a temperature sensor (16), for example, as shown in FIG. 9, described later, whereby the hybridization and elongation can be achieved with a high degree of accuracy on the insulation film (2) of the gene detection field-effect device (1A).

The nucleic acid is charged in negative under an adequate pH condition of buffer solution used for the reaction. Therefore, by forming the double strand and accelerating the elongation as described above, the negative electric charge on the surface of the insulation film (2) is increased and, consequently, the density of carriers, that is, electrons (8) on the surface of the semiconductor substrate (3) formed of silicon or the like is changed by an electrostatic interaction. By detecting the electric signal in association with the change of density of the electrons (8), analysis of SNP can be performed with high degree of sensitivity and high degree of accuracy.

The output value of the gene detection field-effect device (1A) according to the invention in this application depends on pH of the buffer liquid and, in particular, when the value of pH is 7 or lower, a significant difference is achieved, and it is preferable to set the pH to 4 or lower in order to obtain a high signal/noise ratio (S/N ratio).

Figure 2:
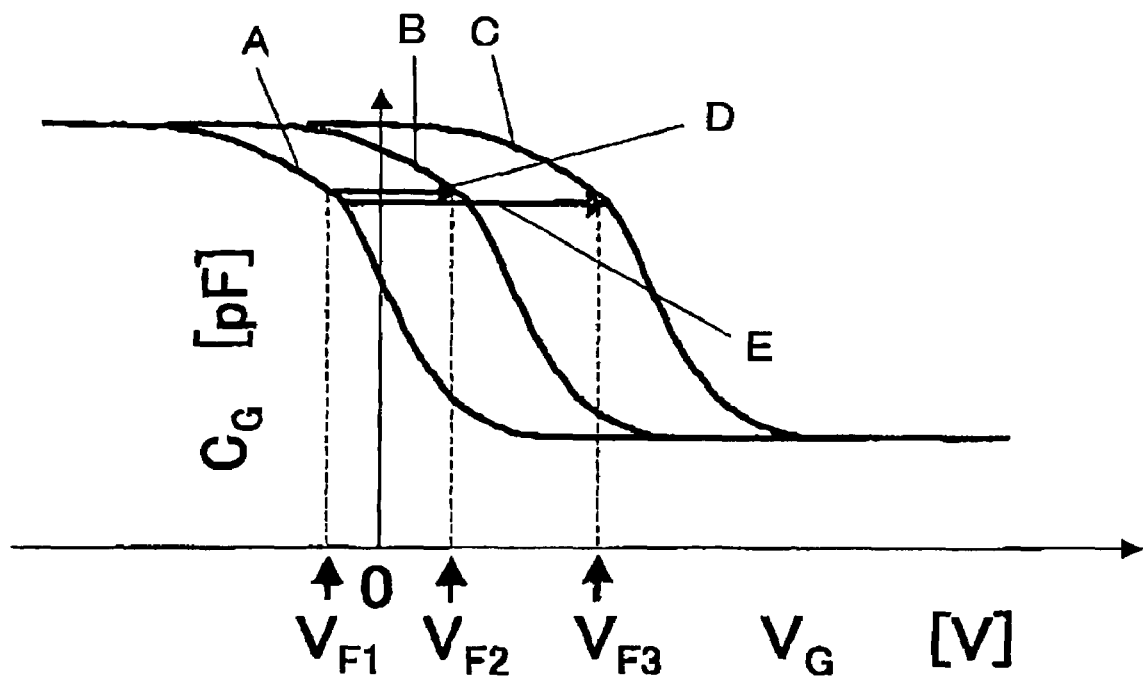
FIG. 2 is a graph schematically showing a detection principle of the gene detection field-effect device in FIG. 1.

FIG. 2 is a conceptual drawing showing an example of detection of the change in density of the carrier on the surface of the semiconductor substrate as a change in capacitance of the gene detection field-effect device.

FIG. 2 is a drawing showing a state of change in capacitance potential characteristic when the reference electrode and the electric terminal of the semiconductor substrate (silicon) are connected to a capacitance meter, and a minute (on the order of 50 mV) voltage of a frequency between several Hz to 1 mHz is superimposed and applied while sweeping a voltage Vc.

When p-type silicon is employed, a capacity of depleted layer on the surface of the semiconductor substrate is changed in association with the change in $V_G$, and the whole capacitance $C_c$ to be measured is a sum of the capacity of the insulation film and the capacitance of the depleted layer on the surface of the semiconductor substrate. Therefore, a characteristic indicated by a reference sign A in the drawing is observed. A voltage at which the energy band in the silicon in the semiconductor substrate becomes flat is referred to as flat band voltage, and serves as an index for characterizing the capacitance potential characteristic. The flat band voltage of the capacitance potential characteristic indicated by the reference sign A is indicated by $V_{F1}$. When the nucleic acid probe and the target gene are hybridized and forms the double strand on the surface of the insulation film, the density of the negative electric charge on the surface increases. Therefore, the capacitance potential characteristic is shifted in the positive direction along a voltage axis, and exhibits a characteristic indicated by a reference sign B in the drawing. The shift amount of flat band voltage $\Delta V_F = V_{F2} - V_{F1}$ (arrow D), where $V_{F2}$ is the flat band voltage at this time, depends on the change in electric charge density on the surface of the insulation film. Therefore, hybridization can be verified by measuring $\Delta V_F$.

In addition, when the DNA is elongated on the surface of the insulation film, the length of the double strand is increased. Therefore, the negative electric charge on the surface is further increased. In other words, the capacitance potential characteristic is shifted in the positive direction, and a characteristic indicated by a reference sign C in the drawing is observed. The amount of shift of the flat band voltage $\Delta V_F = V_{F3} - V_{F1}$ (arrow E), where $V_{F3}$ is the flat band voltage at this time, becomes an index of the change in electric charge density due to the elongation, and is larger than the amount of shift when only the hybridization is performed, whereby measurement with high degree of sensitivity is enabled.

Figure 3:
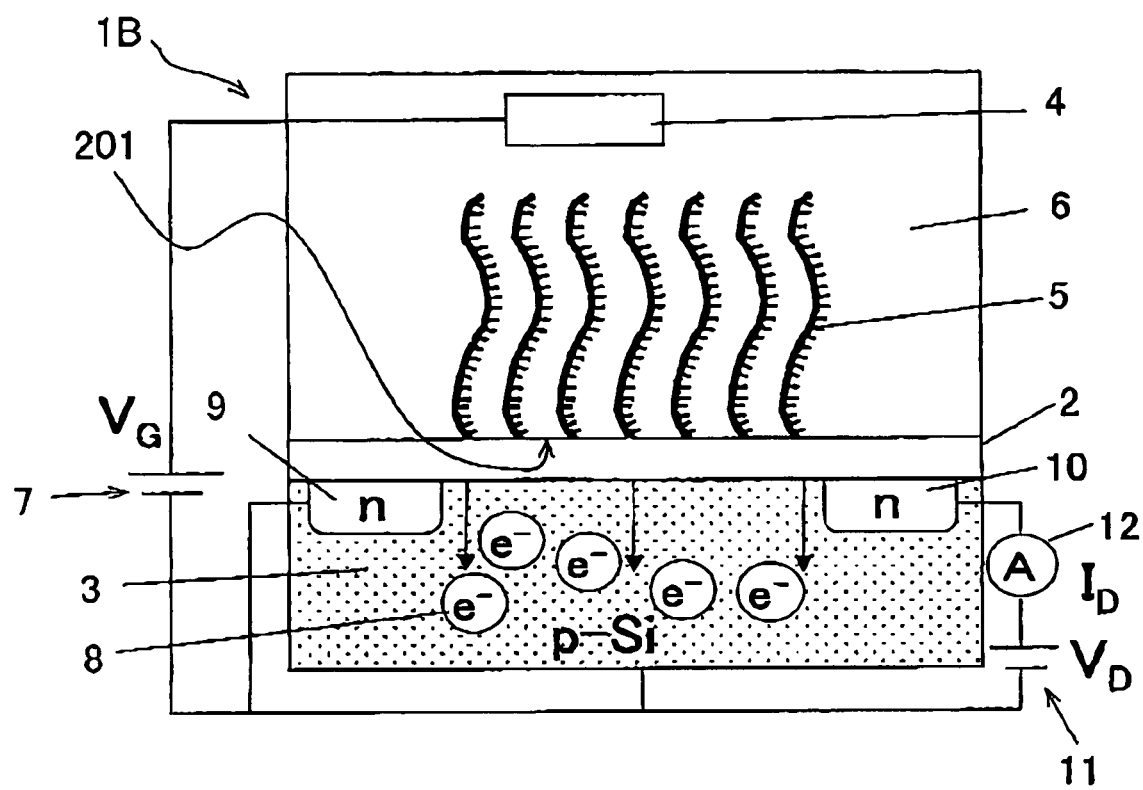
FIG. 3 is a cross-sectional pattern diagram showing an example of a gene detection field-effect transistor according to the gene detection field-effect device in the invention in this application.

FIG. 3 is a cross-sectional pattern diagram showing the gene detection field-effect device (1A) in which a source n-type area (9) and a drain n-type area (10) are formed as a source and a drain in the vicinity of a surface of a p-type silicon (p-Si) as the semiconductor substrate (3) to configure a gene detection field-effect transistor (1B) in the gene detection field-effect device (1A) exemplified in FIG. 1. The gene detection field-effect transistor (1B) may be represented simply as the gene detection field-effect device (1A).

As shown in FIG. 3, a drain electrode (11) for applying a voltage $V_D$ between the source n-type area (9) and the drain n-type area (10) is provided, and an electric current $I_D$ which flows at that time between the source n-type area (9) and the drain n-type area (10) is measured by a drain ampere meter (12). The nucleic acid probe (5) is immobilized on the surface of the insulation film (2) between the source n-type area (9) and the drain n-type area (10) (hereinafter, this area may be expressed as "gate insulation film area (201)"). When the target gene to be detected and analyzed is contained in the sample solution (6) and the nucleic acid probe (5) having the base sequence which is complementary with the target gene is immobilized on the gate insulation film area (201) of the gene detection field-effect transistor (1B), the target gene and the nucleic acid probe (5) are hybridized and form the double strand.

Then, as in the examples shown in FIG. 1 and FIG. 2, the negative electric charge on a surface of the gate insulation film area (201) is increased by the formation of the double strand by hybridization and, consequently, the density of the electrons (8) on the surface of the semiconductor substrate changes by the electrostatic interaction, and the electric signal in association therewith is detected.

Figure 4:
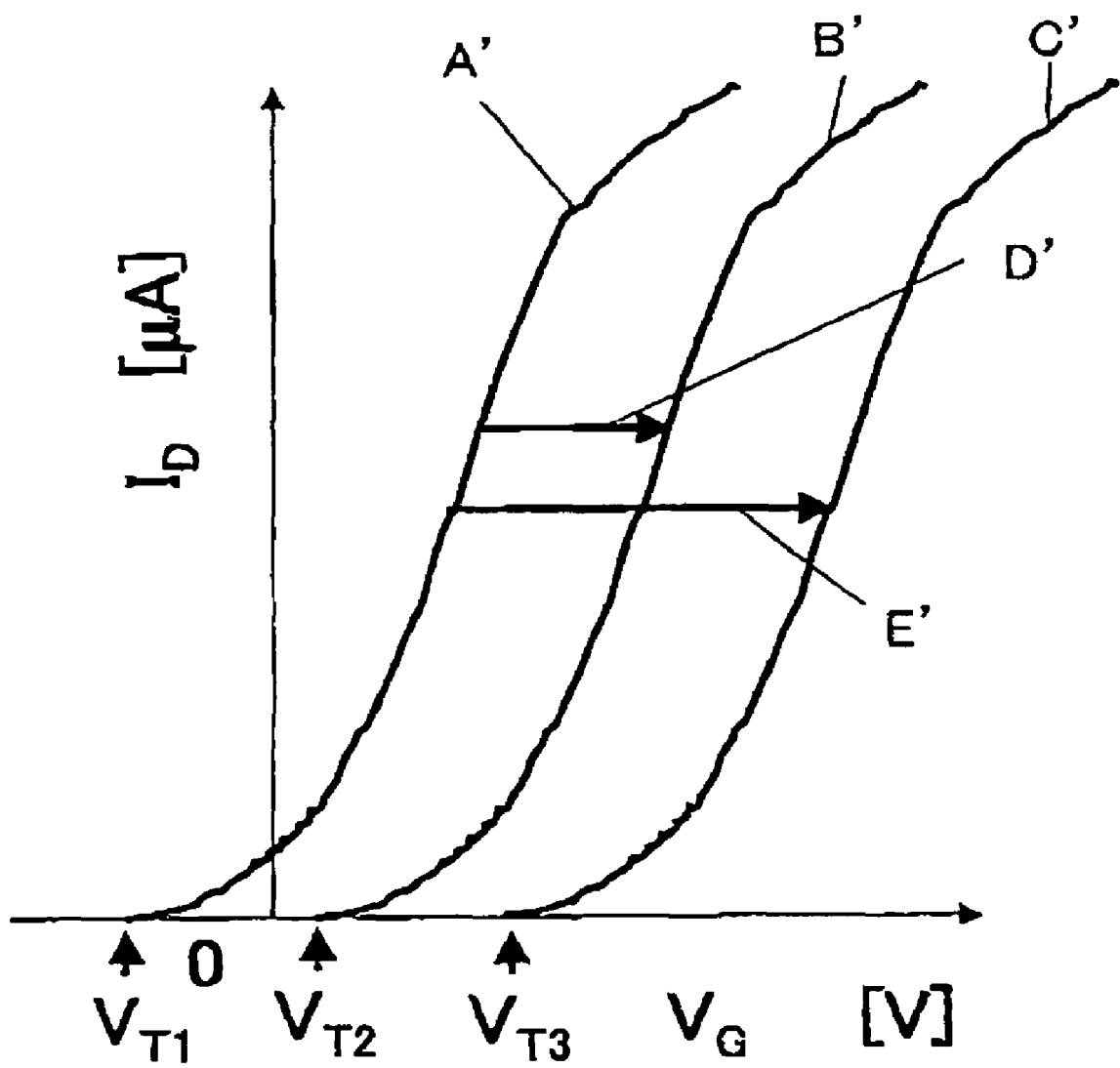
FIG. 4 is a graph schematically showing a detection principle of the gene detection field-effect transistor in FIG. 3.

FIG. 4 is a conceptual drawing showing an example in which the change in density of the carriers on the surface of the semiconductor substrate is detected as the change in the gate voltage $V_G$-drain current $I_D$ characteristic of the gene detection field-effect device. When a negative voltage is applied to the gate voltage $V_G$ in a state in which the constant voltage $V_D$ is applied between the source and the drain, the electrons which are minority carriers are disappeared from the surface of the p-type semiconductor substrate by the electrostatic interaction, and holes as majority carriers are accumulated. On the other hand, since the source and the drain are the n-type areas, when the voltage $V_D$ is applied between the source and the drain, a voltage in the reverse direction from the pn coupling is absolutely applied to any one of the source and the drain. Therefore, the drain current $I_D$ does not flow (negligibly small).

When the gate voltage $V_G$ is gradually increased, the electrons are induced by the surface and the density of electrons on the surface is increased. When a sufficient magnitude of the gate voltage $V_G$ is applied, the n-type areas of the source and the drain are connected by a layer of electrons induced on the surface of the semiconductor substrate, and the drain current $I_D$ flows out while demonstrating a high conductivity. The gate voltage $V_G$ when the drain current $I_D$ is flowed out is referred to as a threshold voltage $V_T$, and serves as an index for characterizing the $V_G$-$I_D$ characteristic. When the gate voltage $V_G$ is applied in the positive direction, the density of electrons on the surface of the semiconductor substrate increases, and the drain current $I_D$ also increases. Therefore, a characteristic indicated by reference sign A' in FIG. 4 is achieved, and a threshold voltage at this time is indicated by $V_{T1}$. When the double strand is formed by the nucleic acid probe and the target gene being hybridized on the surface of the gate insulation film, the density of the negative electric charge on the surface is increased. Therefore, the $V_G$-$I_D$ characteristic shifts in the positive direction along the voltage axis, and a characteristic indicated by reference sign B' in FIG. 4 is achieved. The shift amount of the threshold value, $\Delta V_T = V_{T2} - V_{T1}$ (arrow D'), where $V_{T2}$ is the threshold voltage at this time, depends on the change in density of the electric charge on the surface of the gate insulation film area. Therefore, the hybridization can be verified by measuring the value $\Delta V_T$. In addition, when the DNA is elongated on the surface of the gate insulation film area, the length of the double strand increases, and hence the negative electric charge on the surface is further increased. Therefore, the $V_G$-$I_D$ characteristic is shifted further in the positive direction, and a characteristic indicated by reference sing C' in FIG. 4 is achieved. The shift amount of the threshold voltage $\Delta V_T = V_{T3} - V_{T1}$, where $V_{T3}$ is the threshold voltage at this time, serves as an index of change in density of electric charge as a result of elongation, and the shift amount is larger than the case in which only the hybridization is performed. Therefore, measurement, that is, detection with high degree of sensitivity is enabled.

Figure 5:
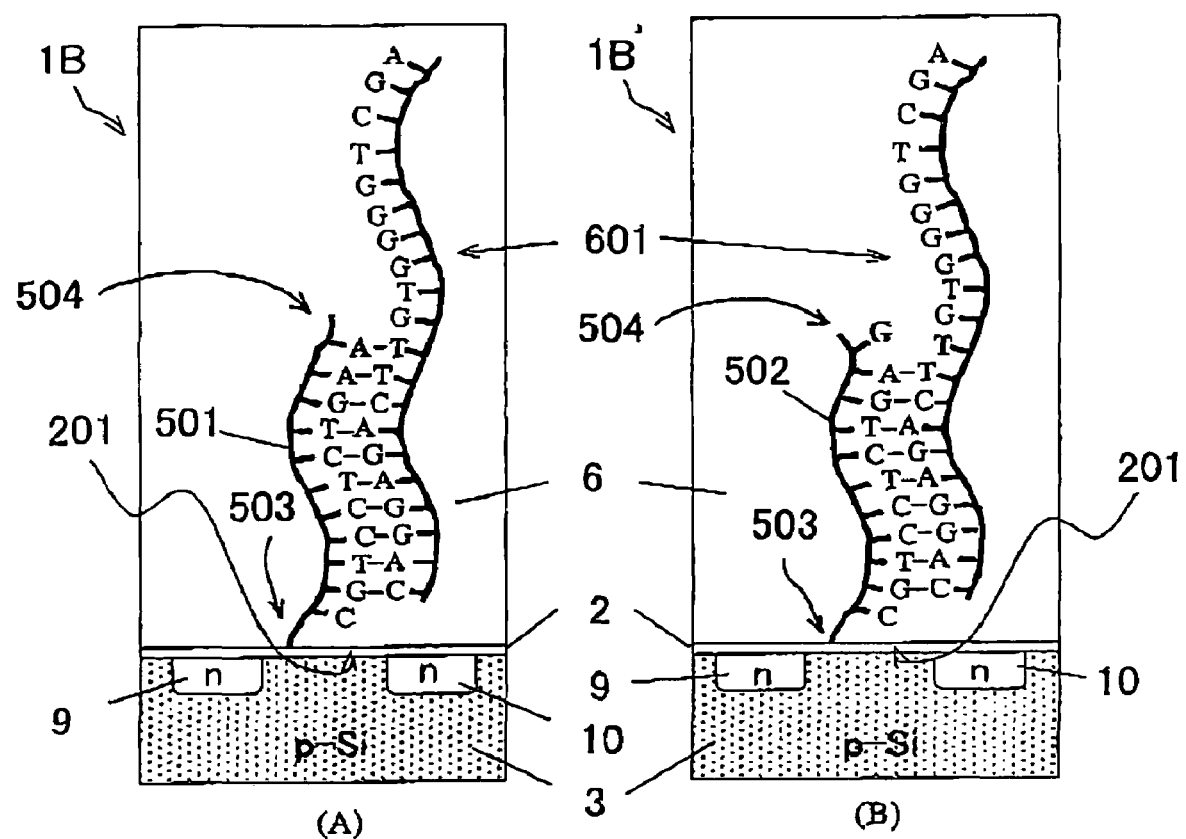
FIG. 5 is a cross-sectional pattern diagram showing a state in which a nucleic acid probe in which one base is different is immobilized in the gene detection field-effect transistor composed of the gene detection field-effect device according to the invention in this application, in which (A) is a gene detection field-effect transistor to which a wild-type nucleic acid probe is immobilized, (B) is a gene detection field-effect transistor to which a mutant-type nucleic acid probe is immobilized.

FIG. 5 a cross-sectional pattern diagram showing a state in which two of the gene detection field-effect devices (1B) composed of the gene detection field-effect device (1A) according to the invention in this application are provided, and the different nucleic acid probes (5) are immobilized respectively on the gene detection field-effect devices (1B) to be hybridized with a target gene (601), in which (A) is a state in which the nucleic acid probe (wild-type) nucleic having the base sequence which is completely complementary with the base sequence of the target gene is immobilized, and (B) shows a state in which the nucleic acid probe (mutant-type) in which only one base is different from the base sequence of the target gene is immobilized.

Figure 6:
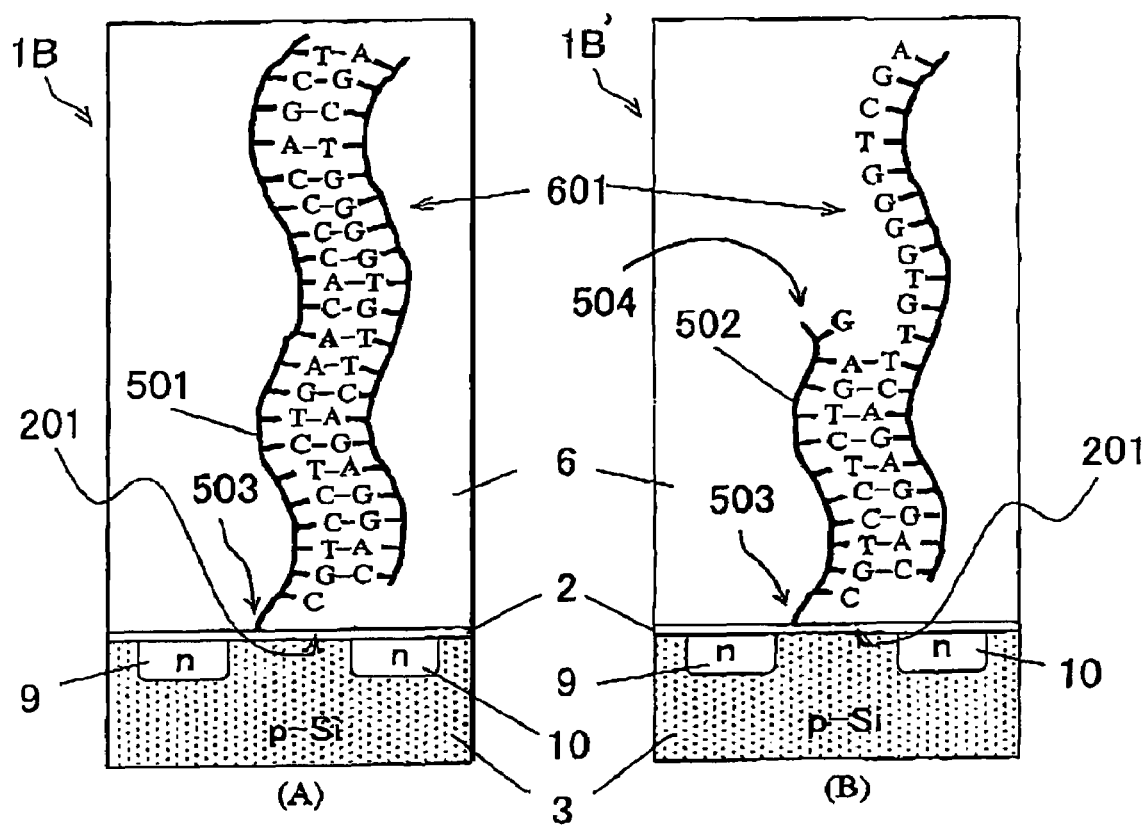
FIG. 6 is a cross-sectional pattern diagram showing states of elongation in the respective gene detection field-effect transistors shown in FIG. 5, in which (A) is a gene detection field-effect transistor to which a wild-type nucleic acid probe is immobilized, (B) is a gene detection field-effect transistor to which a mutant-type nucleic acid probe is immobilized.

FIG. 6 is a cross-sectional pattern diagram showing a state in which elongation is accelerated in the example shown in FIG. 5, in which (A) shows a state in which the target gene and the nucleic acid probe are elongated, and (B) shows a state in which the elongation of the target gene and the nucleic acid probe is stopped. The basic configurations in FIG. 5 and FIG. 6 are substantially the same as the example in FIG. 3.

As shown in FIG. 5 and FIG. 6, according to the invention in this application, by employing the gene detection field-effect transistor (1B) in which at least two of the gene detection field-effect transistors (1B) are provided and at least two types of the nucleic acid probes (5) are immobilized on the insulation films (2) of the respective gene detection field-effect transistors (1B), analysis of the SNP can be achieved with a high degree of sensitivity and a high degree of accuracy as described above.

At least two types of the nucleic acid probes (5) described above mean a wild-type (normal type) nucleic acid probe (501) having the base sequence which is complementary with the base sequence of the target gene (601) as a target of analysis and a mutant-type nucleic acid probe (502) having the base sequence which is not complementary with the base sequence of the target gene (601) (In other words, the wild-type (normal type) nucleic acid probe (501) having a base sequence which is complementary with the wild-type (normal type) base sequence of the target gene and the mutant-type nucleic acid probe having a base sequence which is complementary with the mutant-type nucleic acid probe of the target gene). The mutant-type nucleic acid probe (502) is preferably configured in such a manner that the base at the end on the opposite side from an immobilized end (503) which is an end to which the nucleic acid probe (5) is immobilized on the insulating film (2), that is, at a non-immobilized end (504), which is an end of the nucleic acid probe (5) not immobilized is different from the base at the non-immobilized end (504) of the wild-type nucleic acid probe (501). In the example shown in FIG. 5(B), the base at the non-immobilized end (504) of the mutant-type nucleic acid probe (502) is "G", and the base of the target gene corresponding to this position is "T". Therefore, the hybridization is stopped halfway, and the double strand cannot be formed. On the other hand, the base at the non-immobilized end (504) of the wild-type nucleic acid probe (501) is "A", which has a complementary relation with the base "T" of the target gene corresponding to this position, so that they are hybridized and form the double strand.

Then, the sample solution (6) containing the base sequence of the target gene (601) is introduced on the insulation film (Z) of the field-effect device (1B) composed of the gene detection field-effect device (1A) to cause hybridization and washes the target gene (601) before reaction with buffer solution or the like. Subsequently, a process of molecular biological reaction such as the elongation of DNA or a reaction with the intercalator molecule are effected continuously on the surface of the insulation film (2) using deoxyadenosine triphosphoric acid (dATP), deoxyguanosine triphosphate (dGTP), deoxycytidine triphosphate (dCTP), and deoxythymidine triphosphate (dTTP) as ground substances along with DNA synthetic enzyme such as Taq DNA polymerase or the like to wash the enzyme or the ground substance not reacted. Consequently, using the field-effect of the change in density of electric charge on the surface generated by the DNA elongation or the like, the change in density of the electrons (8) electrostatically induced on the surface of the semiconductor substrate (3) is detected.

In order to achieve the measurement with high degree of sensitivity by increasing the change in density of electric charge on the surface, a phenomenon of hybridization can be detected with a large signal/noise ratio (S/N ratio) by increase in negative electric charge caused by elongation of the nucleic acid, enhancement of the signal caused thereby, introduction of the positive electric charge achieved by the reaction with the intercalator, and so on in addition to the negative electric charge which is possessed by the target gene (601) by itself. In other words, the gene type (that is, SNP) of the target gene (601) as the object of analysis can be analyzed by comparing the outputs from the respective gene detection field-effect devices (1A).

When designing the base sequence of the nucleic acid probe (5) to be immobilized on the surface of the insulation film (2), as described above, the position of the mutation is set to the non-immobilized end (504) as an end on the opposite side from an immobilized end (503) with respect to the surface of the insulation film (2). Then, the wild-type nucleic acid probe (501) corresponding to the wild (normal) type in the SNP of the target gene (601) and the mutant-type nucleic acid probe (502) corresponding to the mutant-type are immobilized separately to cause hybridization simultaneously for one type of sample solution (6) for achieving elongation, so that the single nucleotide polymorphism (SNP) can be measured with high degree of accuracy.

In addition, by setting the temperature at the time of hybridization to a dissociation temperature (Tm) of the wild-type nucleic acid probe (501) or the mutant-type nucleic acid probe (502), the selectivity of the hybridization can be improved, and by causing the elongation, the specificity of the reaction can further be enhanced, whereby the SNP analysis with higher degree of accuracy is achieved.

This is because hydrophilic property between bases is low in the hybridization with a mismatched mutant-type nucleic acid probe (502) which includes the mutation at an end, and hence sufficient hybridization is not achieved, whereby elongation does not occur. On the other hand, in the case of the fully matched wild-type nucleic acid probe (501), the bases at the non-immobilized ends surely form the double strand by hydrogen bonding, and hence the elongation occurs, whereby the negative electric charge increases. Accordingly, the density of electrons (8) on the surface of the semiconductor is changed with the electrostatic interaction, and by measuring the change in electric characteristic in association therewith, the SNP can be analyzed with high degree of accuracy.

In other words, the method of analyzing gene polymorphism according to the invention in this application is, in particular, as regards the measurement of the output value, based on measuring a differential output value V1 between the first gene detection field-effect transistor (1B) in which the wild-type nucleic acid probe (501) is immobilized (gene detection field-effect device), and a third gene detection field-effect transistor (not shown) in which no nucleic acid probe is immobilized on the insulation film (gene detection field-effect device), and a differential output value V2 between a second gene detection field-effect transistor (1B') in which the mutant-type nucleic acid probe (502) is immobilized (gene detection field-effect device) and the third gene detection field-effect transistor (gene detection field-effect device), and displaying three patterns classified on the basis of the measurements, including a pattern in which V1 is larger than V2 (V1>V2), a pattern in which V1 and V2 are almost the same (V1≈V2), and a pattern in which V1 is smaller than V2 (V1<V2) is performed and displayed.

Figure 7:
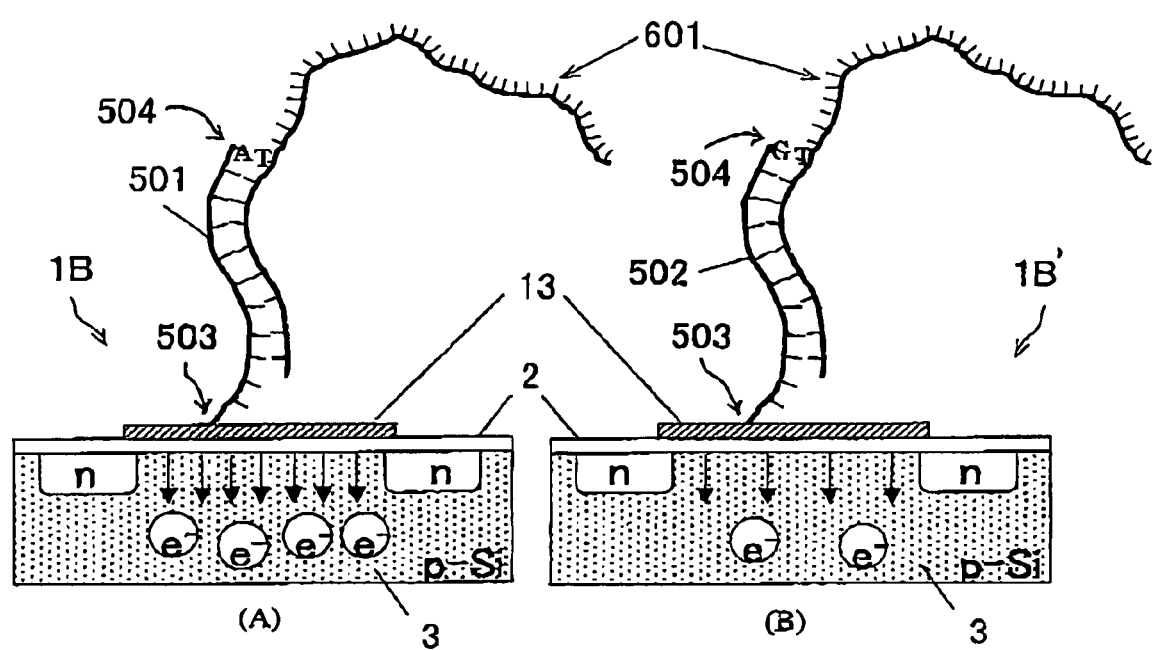
FIG. 7 is a cross-sectional pattern diagram showing a state in which the nucleic acid probe is immobilized via a metal electrode in the gene detection field-effect device composed of the gene detection field-effect device according to the invention in this application, in which (A) shows a gene detection field-effect transistor to which the wild-type nucleic acid probe is immobilized and (B) shows a gene detection field-effect transistor to which the mutant-type nucleic acid probe is immobilized.

FIG. 7 is a cross-sectional pattern diagram showing a state in which the nucleic acid probe (5) is immobilized on the insulation film (2) via a metal electrode (13) in the invention in this application. The metal electrode (13) may be formed of white gold, gold, silver, palladium, titan, chrome, and so on as described above, whereby the change in electric characteristic in association with the change in density of the electrons (8) can be detected with higher degree of accuracy.

Figure 8:
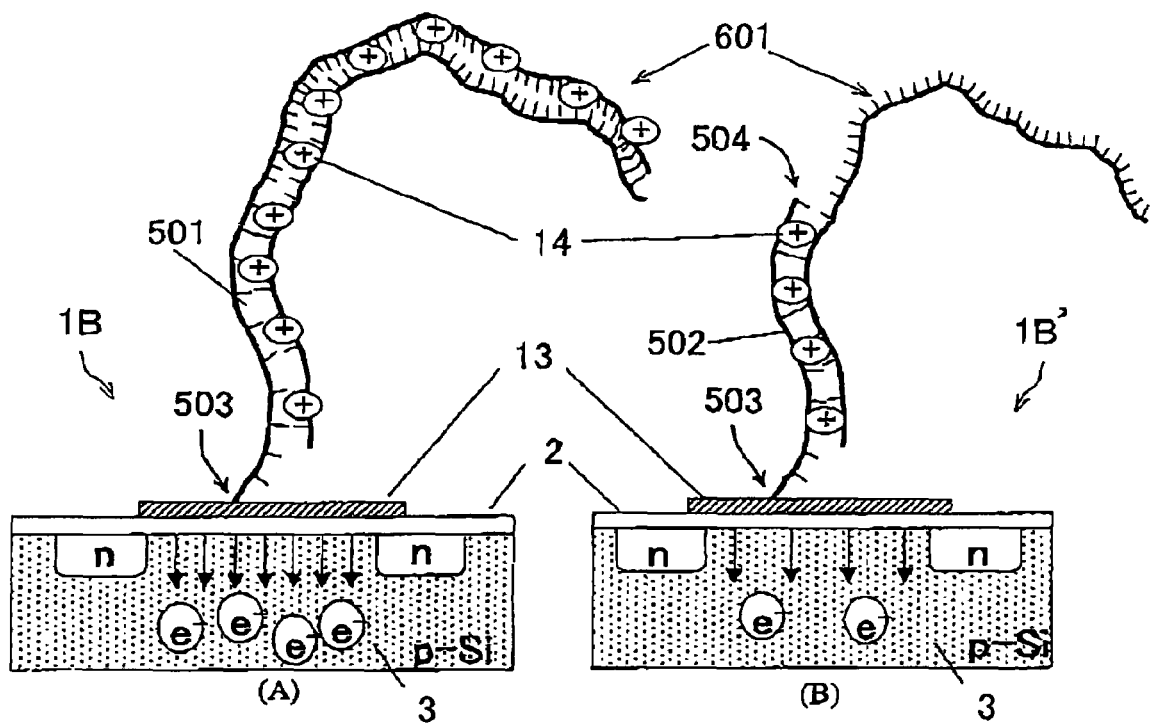
FIG. 8 is a cross-sectional pattern diagram showing a state in which an intercalator is caused to produce a response with the nucleic acid probe in FIG. 7, in which (A) shows a gene detection field-effect transistor to which the wild-type nucleic acid probe is immobilized and (B) shows a gene detection field-effect transistor to which the mutant-type nucleic acid probe is immobilized.

FIG. 8 is a cross-sectional pattern diagram showing a state in which an intercalator (14) caused to produce a response in the invention in this application.

The intercalator (14) reacts only with the double strand nucleic acid, and is ionized and positively charged in the solution. Therefore, using this property, when the intercalator (14) is introduced, it reacts more with the double strand nucleic acid of the gene detection field-effect transistor (1B) on which the wild-type nucleic acid probe (501) which is elongated by the elongation is immobilized, and hence a large signal change is obtained, which is to be detected. As the intercalator (14), for example, Hoechst33258, ethidium bromide, Cyber Green, or Pico Green can be employed.

FIG. 9 is a cross-sectional pattern diagram showing another embodiment of the invention in this application. The basic configuration or the like are substantially the same as the examples shown in FIG. 3, FIG. 5, or FIG. 6.

In the invention in this application illustrated in FIG. 9, the heater (15) as an n-type area for a heater is formed as temperature control means for accelerating the elongation of the nucleic acid and the temperature sensor (16) is formed as a pn coupling for a temperature sensor on the semiconductor substrate (3) on which the gene detection field-effect transistor (1B) illustrated in FIG. 3, FIG. 5 or FIG. 6. In this case, a plurality of p-wells (17) are formed on one semiconductor substrate (3) and the heater (15) and the temperature sensor (16) are integrated. The wild-type nucleic acid probe (501) and the mutant-type nucleic acid probe (502) are immobilized respectively on a gate insulation film area (201) of the gene detection field-effect transistor (1B) so that the hybridization with the target gene (601) in the sample solution (6) and elongation are accelerated, and hence the SNP analysis with high degree of accuracy is achieved. In this case, the heater (15) and the temperature sensor (16) were operated and the temperature of the sample near the semiconductor substrate (3) was set and controlled to 45° C. at the time of hybridization and to 62° C. at the time of elongation. By integrating the heater (15) and the temperature sensor (16) on the gene detection field-effect transistor (1B) as the temperature control means as described above, the temperatures at the time of hybridization and elongation can be set to optimal values, whereby measurement with higher degree of accuracy is achieved.

Figure 10:
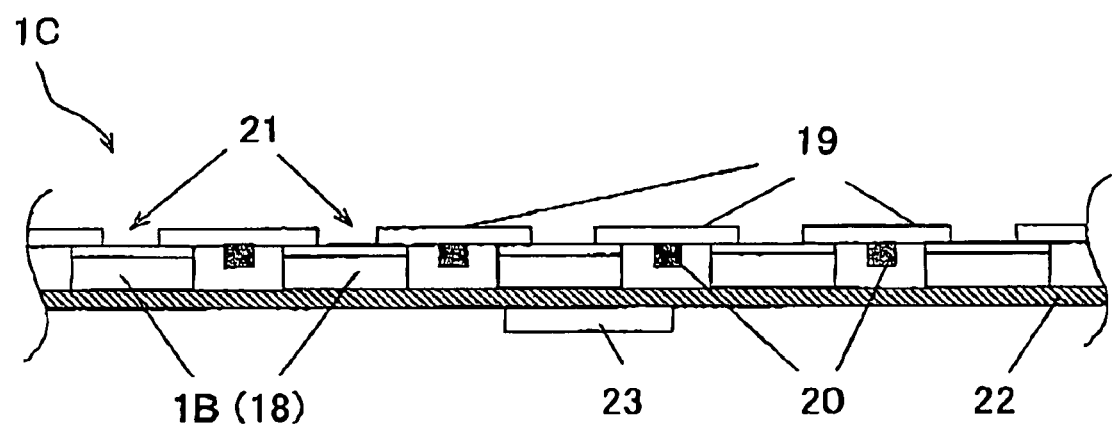
FIG. 10 is a cross-sectional pattern diagram showing an embodiment in which the gene detection field-effect transistor composed of the gene detection field-effect device according to the invention in this application is formed into an array.

FIG. 10 is a cross-sectional pattern diagram showing a structure in which the embodiment in FIG. 9 is formed into an array to enable a plurality of SNP analyses.

As illustrated in FIG. 10, the respective semiconductor substrates (3) on which the gene detection field-effect transistors (1B) are formed are arranged one of the surfaces of an insulation film (19) so as to be capable of setting the temperatures thereof to optimal temperatures corresponding to the dissociation temperature of the nucleic acid probe (5), so that heat is efficiently radiated via the insulation film (19). In addition, a structure in which the respective gene detection field-effect transistors (1B) (silicon substrates (18)) are surrounded by heat-conductive substance (20) such as silicone or polysilicon is employed in order to reduce the temperature cross-talk among the respective semiconductor substrates (3) and enable independent temperature control, thereby allowing beat to be radiated efficiently via the beat-conductive substance (20).

In order to introduce the sample solution containing the target gene on the gene detection field-effect transistors 1B, openings (21) are formed on the insulation film (19) and the gene detection field-effect transistors (1B) are aligned so as to match the openings (21) of the insulation film (19). In addition, with the provision of a Pertier element (23) bonded to a copper plate (22) on a back surface of the copper plate (22), accuracy of temperature control can be improved, and the time required for cooling can be reduced. With a gene detection field-effect transistor array (1C) having such a structure, analysis with high degree of accuracy can be performed in parallel in the plurality of SNPs, and a high-throughput analyzing system can be established.

Figure 11:
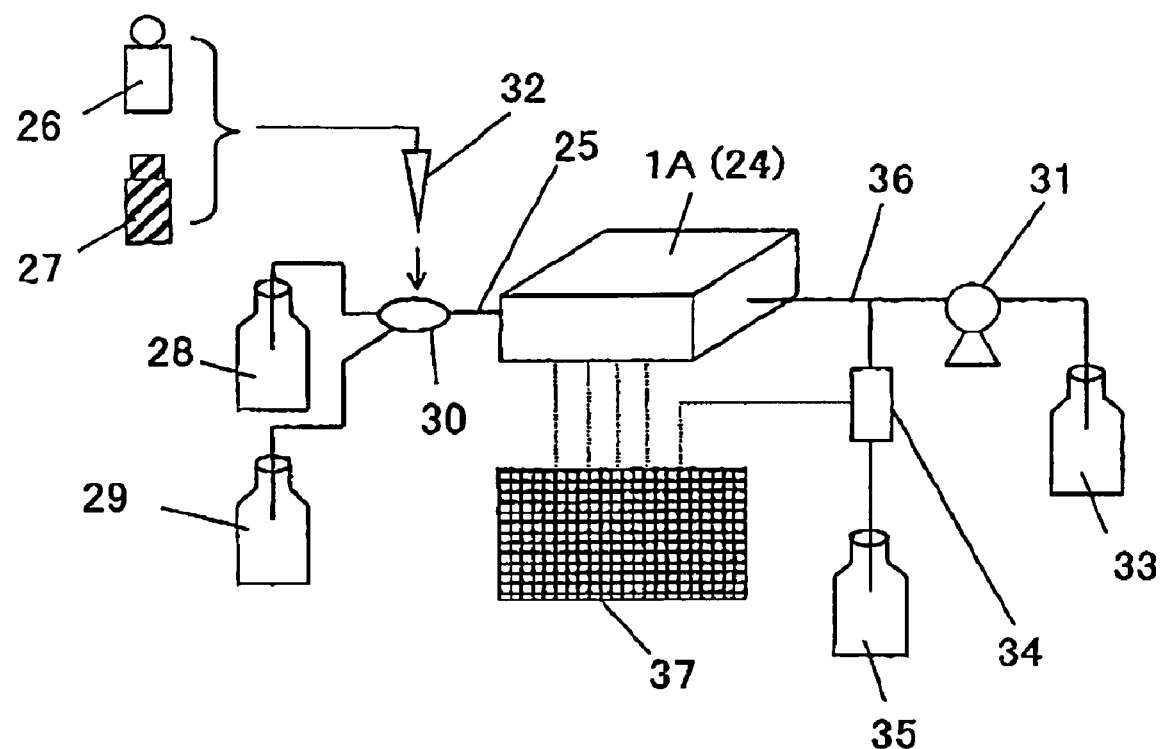
FIG. 11 is a schematic pattern diagram showing an entire configuration of a measuring system using the gene detection field-effect device according to the invention in this application.

FIG. 11 is a conceptual pattern diagram showing an example of a measuring system using the gene detection field-effect device (1A) according to the invention in this application.

In other words, according to the invention in this application, the gene detection field-effect device (1A) having the characteristic as described above (or the gene detection field-effect transistor) is mounted to a flow cell (24) and connected to a flow channel (25) as shown in FIG. 11. Buffer liquid (28) and cleaning liquid (29) are connected to the flow channel (25) via a valve (30), and the buffer liquid (28) and the cleaning liquid (29) can be introduced in the flow cell (24) by driving a pump (31). A sample (26) and Taq DNA polymerase as enzyme for elongation and reagent (27) such as dATP, dGTP, dCTP, dTTP, as the ground substance are dispensed into the valve (30) with a dispenser (32), and is introduced into the flow cell (24), so as to cause the same to produce a response with the gene detection field-effect device (1A) (gene detection field-effect transistor).

After the reaction, the used liquid is transferred to a waste liquid bottle (33) by the pump (31). Ag—AgCl electrode is used as a reference electrode (34), 3M KDl solution (35) is passed therethrough and is connected to the flow channel (25) on the downstream side of the flow cell (24), where a liquid-liquid coupling (36) is formed and is electrically connected to the gene detection field-effect device (1A) (gene detection field-effect transistor). The output of the gene detection field-effect device (1A) after reaction (gene detection field-effect transistor) is processed/calculated by a signal processing circuit (37).

Figure 12:
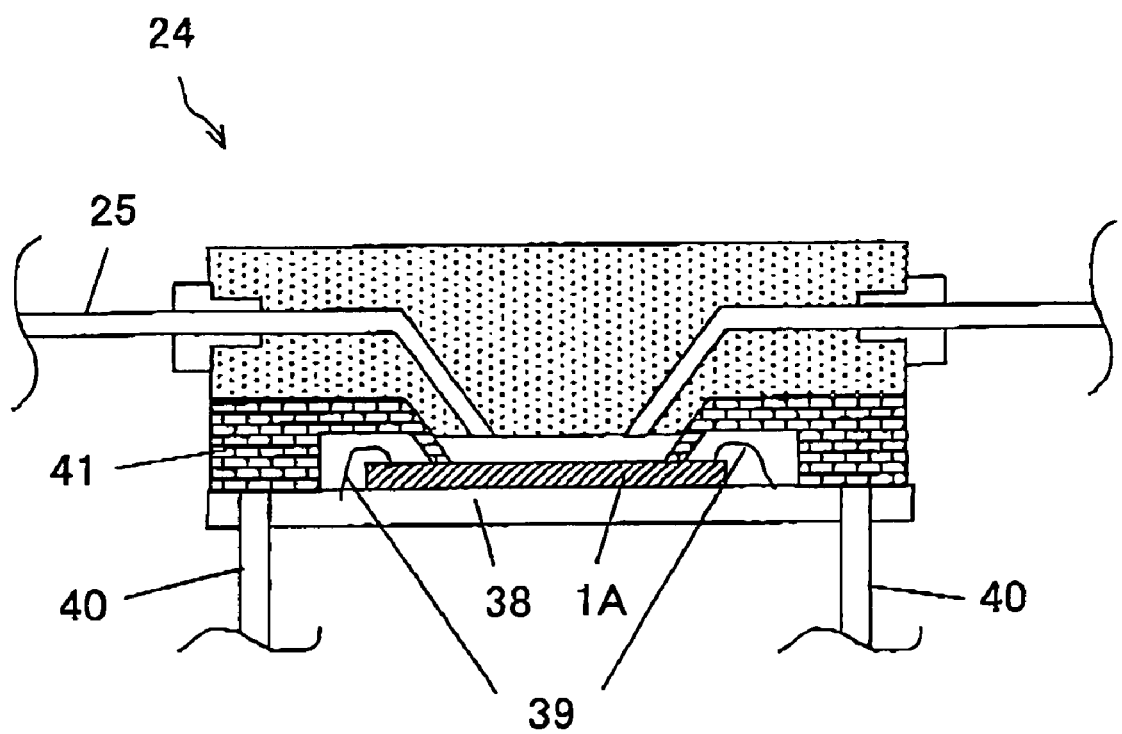
FIG. 12 is a cross-sectional pattern diagram showing a flow cell for mounting the gene detection field-effect device according to the invention in this application.

FIG. 12 is a schematic drawing of a structure of the flow cell (24) illustrated in FIG. 11. The gene detection field-effect device (1A) is mounted to a printed board (38) in the flow cell (24), and is electrically connected to the printed board (38) with a wire (39). A pin (40) is provided on the printed board (38), and is connected to the signal processing circuit (37) illustrated in FIG. 11. The sample solution is introduced into the gene detection field-effect device (1A) through the flow channel (25) (or to the gene detection field-effect transistor). The wire (39) portion is protected by a protection cap (41) so that the sample solution does not come into contact with the wire (39) as the signal transmitting line. The material of the protection cap (41) is not specifically limited as long as it has an insulating property, and preferably, materials, for example, acryl, polypropylene, polycarbonate, are suitable.

Since the measuring system in which the gene detection field-effect device (1A) in this configuration is used employs a measurement of a flow system, a number of samples can be processed continuously and automatically, and hence it is effective for a measurement of a high throughput.

Figure 13:
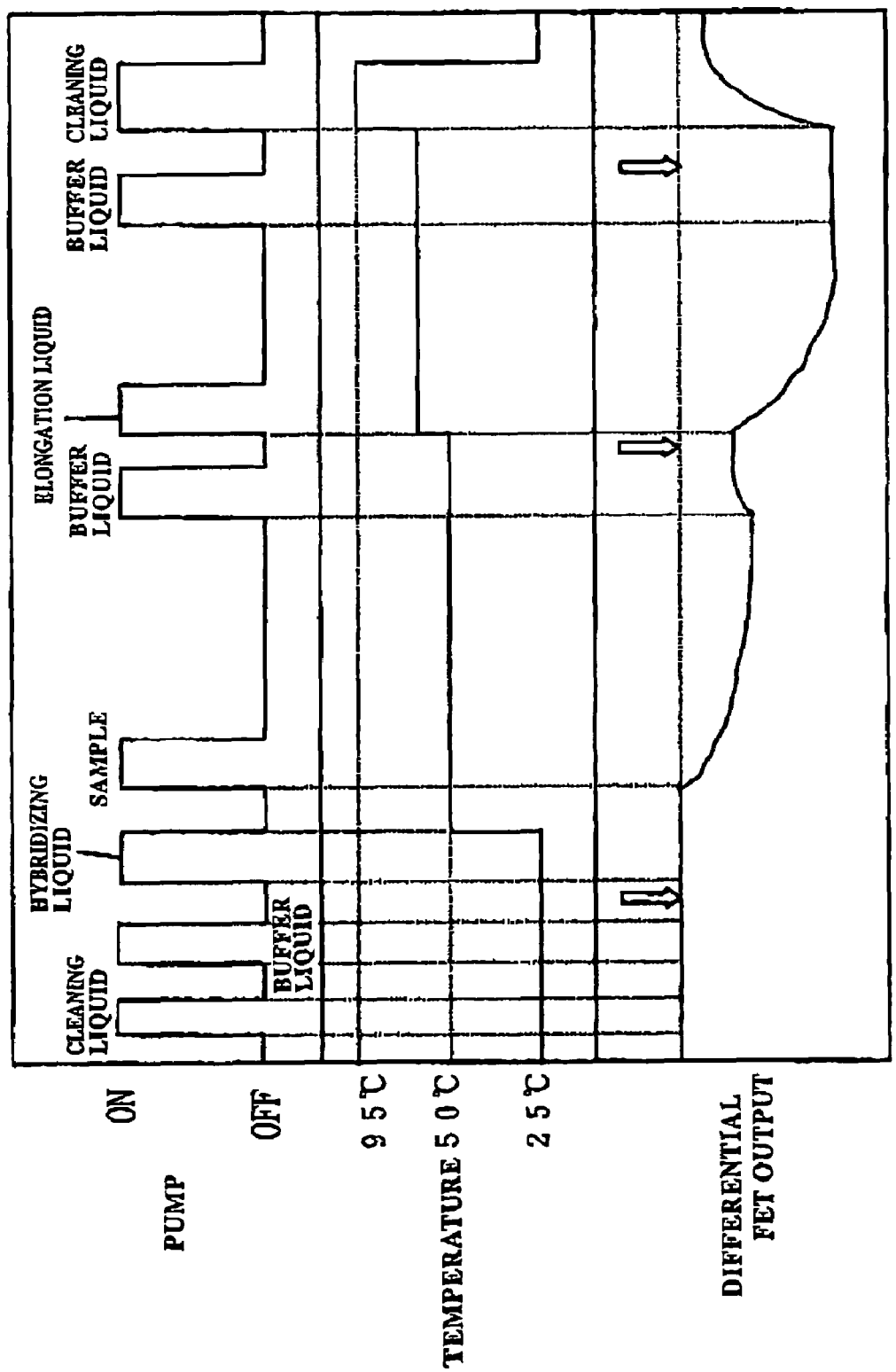
FIG. 13 is a schematic explanatory drawing showing a measurement protocol according to the gene detection field-effect device according to the invention in this application.

As shown in the examples above, when polymorphism (for example, single nucleotide polymorphism or microsatellite polymorphism) is analyzed using the invention in this application, it is carried out in the following steps, for example, as shown in FIG. 13. That is:

(1) introducing the cleaning liquid to the flow cell;
(2) introducing the buffer liquid to the flow cell (displacement of cleaning liquid)
(3) setting the temperature of the field-effect device to an optimum temperature of the nucleic acid probe;
(4) measuring the output value of the respective gene detection field-effect devices and calculating the differences;
(5) dispensing the sample to the valve, and introducing the hybridization liquid to the flow cell;
(6) hybridizing in the flow cell;
(7) introducing the buffer liquid to the flow cell and removing the sample which is not reacted;
(8) measuring the output value of the respective gene detection field-effect devices and calculating the differences;
(9) introducing Taq polymerase and mixed liquid of dATP, dGTP, dCTP, dTTP as the ground substance to the flow cell and cause the same to be elongated;
(10) introducing the buffer liquid and removing enzyme and the ground substance which is not reacted;
(11) measuring the output value of the respective gene detection field-effect devices and calculating the differences;
(12) setting the sample temperature in the flow cell to 95° C.;
(13) introducing the cleaning liquid and cleaning the inside of the flow cell; and
(14) returning back to the procedure in (1).

Arrows in FIG. 13 indicate timings to read the output potentials.

Subsequently, examples are shown below and the invention in this application will be described further in detail. The following example is not intended to limit the invention in this application as a matter of course.

EXAMPLE

Example 1

Detection and Analysis of SNP in Factor VII Gene

The Factor VII gene as one of blood coagulation genes includes a plurality of single nucleotide polymorphisms (SNP) existing therein. It is known that the wild-type (normal) of one of the SNPs at a position −122 is thymine (T) and the mutant-type thereto is cytosine (C). In order to detect the SNP at the portion −122 of the Factor VII gene, two types of nucleic acid probes formed of 11 bases, which correspond to the wild-type and the mutant-type, respectively were synthesized. The base sequences thereof were as follows, in which a sequence number 1 designates a wild-type nucleic acid probe and a sequence number 2 designates a mutant-type nucleic acid probe.

Wild-type nucleic acid probe: 5'-CGTCCTCTGAA-3' (sequence No. 1)

Mutant-type nucleic acid probe: 5'-CGTCCTCTGAG-3' (sequence No. 2)

In this example, the nucleic acid probes were synthesized so that the base of the SNP portion corresponds to a 3' terminal end of the nucleic acid probe. In other words, the base of the 3' terminal end was adenine (A) in the wild-type nucleic acid probe, and it was guanine (G) in the mutant-type nucleic acid prob. Other base sequences were all the same in the wild-type and in the mutant-type, and hybridization to the Factor VII gene as the object of detection could be carried out.

On the other hand, a 5' terminal end of the nucleic acid probe was modified with the amino group and was immobilized to a surface of the gate insulation film area.

The gate inflation film of the gene detection field-effect transistor in this example was modified with silicon nitride, and the surface thereof was chemically modified with γ-aminopropyl triethoxysilane, and the amino group was introduced to a surface of the nitrided semiconductor substrate. Then, the amino group of the nucleic acid probe and the amino group of silicon nitride were caused to produce a response with, for example, bifunctional reagent such as glutaraldehyde, and formed the coupling by Schiff base, so that the nucleic acid probe was immobilized on the surface of the nitrided semiconductor substrate.

This example was, for example, as shown in FIG. 5, the wild-type nucleic acid probe was immobilized on the surface of the gate insulation film area of one of the gene detection field-effect transistors, and the mutant-type nucleic acid probe was immobilized to the surface of the gate insulation film area of the other gene detection field-effect transistor, and the sample which was amplified by polymerase chain reaction (PCR) in advance was caused to produce a response.

The sample, after having extracted human genome from white blood cell in blood, and having amplified the area of a length of 20 bases including the SNP portion, was introduced into the gene detection field-effect transistor in which the wild-type nucleic acid probe and the mutant-type nucleic acid probe were immobilized, and was subjected to hybridization for 8 hours at 45° C. After hybridization, cleaning with buffer liquid was carried out to remove the sample which was not reacted.

Since the base sequence of the wild-type nucleic acid probe was completely complementary with the base sequence of the wild-type sample, it was completely coupled into complementary strand including the SNP portion to form the double strand DNA. On the other hand, in the case of the mutant-type nucleic acid probe, since the base at the 3' terminal end was guanine (G), it was not coupled into the complementary strand with base thymine (T) on the wild-type sample nucleic acid, so that the double strand DNA was formed in the shape in which the 3' terminal end was opened. Therefore, the wild-type nucleic acid probe and the mutant-type nucleic acid probe were different in base sequence, the dissociation temperatures (Tm) of both parties were different, and hence the selectivity of the double strand formation could be enhanced by controlling the hybridization temperature.

Subsequently, enzyme Taq DNA polymerase and mixed liquid including dATP, dGTP, dCTP, and dTTP which serve as the ground substance were introduced into the sample, and the elongation were carried out on the gate insulation film at a temperature set to 62° C. As shown in FIG. 6, in the gene detection field-effect transistor in which the wild-type nucleic acid probe was immobilized, since the completely complementary double strand including the terminal end was formed by the introduction of the sample containing the target gene of the wild-type (normal type), the double strand was synthesized by elongation. By this elongation, the output of the gene detection field-effect transistor, in which the wild-type nucleic acid probe was immobilized, was changed by 20 mV. On the other hand, in the gene detection field-effect transistor in which the mutant-type nucleic acid probe was immobilized, since the bases at the 3' terminal ends were not coupled and were in the opened shape, the elongation did not occur. Therefore, the output of the gene detection field-effect transistor in which the wild-type nucleic acid probe was immobilized was little changed (only the change of 1 mV).

On the other hand, when the sample which contained only the mutant-type target gene was introduced, the elongation occurred only in the gene detection field-effect transistor in which the mutant-type nucleic acid probe was immobilized, and the output thereof was change by 18 mV. In this case, the output of the gene detection field-effect transistor in which the wild-type nucleic acid probe was changed by 0.5 mV, which was little. When the sample which contains both the wild-type and the mutant-type object genes was introduced, the outputs of the both gene detection field-effect transistors were changed. The output of the gene detection field-effect transistor in which the wild-type nucleic acid probe was immobilized was changed by 12 mV, and the output of the gene detection field-effect transistor in which the mutant-type nucleic acid probe was immobilized was changed by 10 mV.

From the results shown above, it was found that the SNP of the gene in the sample solution could be detected by designing the nucleic acid probes so that the base at the 3' terminal ends corresponded to the SNP portion, immobilizing the wild-type and mutant-type nucleic acid probes respectively on the gate insulation films on the respective gene detection field-effect transistors, causing the hybridization with the sample solution containing the target gene, and causing the elongation continuously. Furthermore, it was confirmed that a wild-type homozygote, a wild-type and mutant-type heterozygote, and a mutant-type homozygote could be identified by comparing the magnitude of change in output of the gene detection field-effect transistors in which the wild-type and mutant-type nucleic acid probes were immobilized, and hence genotype could be detected.

Example 2

When Peptide Nucleotide Acid, PNA was Used in Detection of SNP in Factor VII Gene In the example 1 shown above, the double strand nucleus acid with higher stability can be formed by using Peptide Nucleotide Acid, PNA as the nucleic acid probe to be immobilized to the gate insulation film area of the gene detection field-effect transistor.

Therefore, in this example, Peptide Nucleotide Acid (PNA) was used as the nucleic acid probe although the basic characteristics are substantially the same as the example 1.

Consequently, in the case of the sample containing the wild-type homozygote, the output of the transistor in which the wild-type PNA probe was immobilized was changed by 23 mV, while the output of the transistor in which the mutant-type PNA probe was immobilized was changed by 4 mV. In the case of the sample containing the wild-type and mutant-type heterozygote, the output of the gene detection field-effect transistors in which the wild-type and mutant-type PNA probes were immobilized were 15 mV, 13 mV respectively, and both the wild-type and mutant-type could be detected.

In the case of the sample containing the mutant-type homozygote, the output of the gene detection field-effect transistor in which the wild-type PNA probe was immobilized was changed by 2 mV, which was little, while the output of the gene detection field-effect transistor in which the mutant-type PNA probe was immobilized was changed by 19 mV.

As described above, it was found that the wild-type homozygote, the wild-type and mutant-type mixed heterozygote, and the mutant-type homozygote could be recognized, and hence the genotype of the target gene could be detected by employing the PNA as the nucleic acid probe.

It means that the PNA, being different from oligonucleotide, cDNA, or the like having the negative electric charge, has no electric charge and is neutral, and hence there is no electrostatic repulsion between the nucleic acid probe and the target gene, so that a strong double strand nucleic acid can be formed on the gate insulation film. It also means that when the differential measurement is carried out using the gene detection field-effect device in which the nucleic acid probe is formed and the gene detection field-effect device for reference in which the nucleic acid probe is not formed, if the PNA having the neutral electric charge is used, there is no change in flat band voltage or threshold voltage between the gene detection field-effect device and the gene reference field-effect device, and hence the differential measurement with high degree of accuracy can be performed and hence it is effective particularly for the gene detection field-effect device of the electric charge detection type.

In the SNP detection and genotyping using the gene detection field-effect transistor and the elongation as in this example, the procession of reaction can be monitored by constantly measuring the electric potential while the respective processes of induction of sample on the gate insulation film, hybridization, and elongation are in process.

Therefore, the completion of reaction can be detected from the change in electric potential, and the SNP detection and the genotyping can be carried out efficiently. In this example, since the synthesis of bases in association with elongation is detected as the amount of increase in electric charge, the nucleic acid can be detected with high degree of sensitivity by optimizing the length of the base of the nucleic acid probe and the sample nucleic acid and the length of the base after elongation and synthesis.

Example 3

SNP Detection of Alcohol Dehydrogenase Related Gene

It is known that there exists the single nucleotide polymorphism (SNP) in the alcohol dehydrogenase related gene. The nucleic acid probe is designed so that the SNP portion corresponds to the base at the 3' terminal end. The base at the SNP portion is thymine (T) in the wild-type and cytosine (C) in the mutant-type, and the base sequences of the nucleic acid probes corresponding thereto are shown below. The wild-type nucleic acid probe in this example is shown by the sequence No. 3, and the mutant-type nucleic acid probe is shown by the sequence No. 4.
The wild-type nucleic acid probe: 5'-CATACACTA-3' (sequence No. 3)
The mutant-type nucleic acid probe: 5'-CATACACTG-3' (sequence No. 4)

In this example, the basic configuration and the procedure of experiment are the same as in the example 1 and the example 2.

In this example, for example, as shown in FIG. 7 described above, the gene detection field-effect transistor in which the wild-type nucleic acid probe shown in (A) was immobilized and the gene detection field-effect transistor to which the mutant-type nucleic acid probe shown in (B) is immobilized, in which the mutant-type nucleic acid probe shown in (B) was immobilized, were employed. In this example, the metal electrode was formed on the gate insulation film of the gene detection field-effect transistor, and the 5' terminal end of the nucleic acid probe was modified with thiol group and was coupled directly to the metal electrode, so that the nucleic acid probe was immobilized on the surface of the gate insulation film. In this example, a structure formed by laminating gold on a chrome thin film was used as the metal electrode.

The sample, after having extracted human genome from white blood cell in blood, and having amplified the area of a length of 100 bases including the SNP portion, was introduced into the gene detection field-effect transistor in which the wild-type or mutant-type nucleic acid probe was immobilized, and was subjected to hybridization for 8 hours at 45° C. After hybridization, cleaning with the buffer liquid was carried out to remove the sample which was not reacted.

Since the sample used in this example was a sample containing only the wild-type target gene, the double strand was formed by the complete complementary coupling with the wild-type nucleic acid probe. On the other hand, since the mutant-type nucleic acid probe included the SNP at the 3' terminal end, it was not coupled into complementary strand, and the double strand was formed in a state in which the 3' terminal end was opened.

Subsequently, the Taq DNA polymerase and mixed liquid including dATP, dGTP, dCTP, and dTTP which serve as the ground substance were introduced into the sample, and the elongation were carried out on the gate insulation film at a temperature set to 62° C., as in Example 1 and Example 2.

In the gene detection field-effect transistor in which the wild-type nucleic acid probe was immobilized, the double strand with the complete complementary strand was formed including the terminal end by introducing the sample which includes only the wild-type target gene as described above. Therefore, the elongation was accelerated, and the output was changed by 28 mV. On the other band, in the gene detection field-effect transistor tin which the mutant-type nucleus acid probe is immobilized, since the base at the 3' terminal end was not coupled and was in the opened state, the elongation did not occur, and the output was little changed (changed only by 3 mV).

The characteristic of this example is in that the intercalator, which reacts with the double strand nucleic acid is introduced after elongation. The intercalator is generally used as fluorescent dye in an experiment in the molecular biology. Many of molecules of intercalator are ionized in the solution and is charged with positive electricity.

In other words, the intercalator in the invention in this application was used for its property as a dye, but for the property as the electric charge. In this example, Hoechst33258 was used as the intercalator.

In other words, after the hybridization and the elongation following thereto, the output potentials of the gene detection field-effect transistors in which the wild-type and mutant-type nucleic acid probes were immobilized respectively were measured, and then Hoechst33258 was introduced on the gate insulation film for reaction.

Then, as shown in FIG. 8 for example, Hoechst33258 as the intercalator reacted only with the double strand nucleic acid, reacted more with the long double strand nucleic acid of the wild-type transistor which was elongated, and caused a significant signal change.

In the case of this example, after the reaction with Hoechst33298, the output potential of the wild-type transistor was changed by 27 mV, and the output potential of the mutant-type transistor was 6 mV. Accordingly, the genotype detection which can recognize three types of samples; SNP detection and a wild-type/wild-type homo, a mutant-type/mutant-type homo, and a wild-type/mutant-type hetero is achieved.

A remarkable characteristic of a method using the intercalator such as Hoechst33258 or the like is, as described above, in that since the intercalator has a positive electric charge, a signal having an opposite polarity from the output change on the basis of the hybridization and the elongation of the nucleic acid which charged with negative electricity is outputted. Since the intercalator reacts only with the double strand nucleic acid, it does not react with the single strand nucleic acid which is non-specifically adsorbed on the gate insulation film, so that the signal on the basis of the hybridization/elongation can be selectively detected by separating the signal on the basis of the hybridization/elongation and the signal of the single strand nucleic acid which is non-specifically adsorbed. Accordingly, the SNP and the genotype can be detected with high signal/noise ratio (S/N ratio).

INDUSTRIAL APPLICABILITY

As described above in detail, according to the invention in this application, detection and analysis of gene with high degree of sensitivity and high degree of accuracy is achieved and, in addition, the gene polymorphism analyzing system in which the size and cost are reduced in comparison with those in the related art is provided.

The invention claimed is:

1. A method of analyzing gene polymorphism using a first, second, and third gene detection field-effect device, wherein each of said first and second gene detection field-effect device is provided with an insulation film including a nucleic acid probe immobilized on one of the surfaces thereof, a semiconductor substrate being installed so as to abut against the other surface of the insulation film, and a reference electrode, and wherein said third gene detection field-effect device is provided with an insulation film free of a nucleic acid probe immobilized on one of the surfaces thereof, a semiconductor being installed so as to abut against the other surface of the insulation film, and a reference electrode;

the method comprising the steps of:

(a) bringing a wild-type nucleic acid probe immobilized to the insulation film of the first gene detection field-effect device into contact with sample solution containing at least one target gene to hybridize the nucleic acid probe and the target gene on the insulation film, bringing a mutant-type nucleic acid probe immobilized to the insulation film of the second gene detection field-effect device into contact with sample solution containing the at least one target gene to hybridize the nucleic acid probe and the target gene on the insulation film, and bringing the insulation film free of nucleic acid probe immobilized thereon of the third gene detection field-effect device into contact with sample solution containing the at least one target gene to hybridize the nucleic acid probe and the target gene on the insulation film;

(b) introducing cleaning liquid on the respective insulation films of the first, second, and third gene detection field-effect devices to remove the target gene which is not reacted;

(c) introducing deoxyadenosine triphosphoric acid (dATP), deoxyguanosine triphosphate (dGTP), deoxycytidine triphosphate (dCTP), and deoxythymidine triphosphate (dTTP) as ground substances onto the respective insulation films of the first, second, and third gene detection field-effect devices along with Taq DNA polymerase as an enzyme for elongation to cause elongation;

(d) introducing cleaning liquid on the respective insulation films of the first, second, and third gene detection field-effect devices to remove the enzyme and the ground substances which are not reacted; and (e) introducing buffer liquid on the respective insulation films of the first, second, and third gene detection field-effect devices, and measuring a differential output value V1 between the first gene detection field-effect device and the third gene detection field-effect device; measuring a differential output value V2 between the second gene detection field-effect device and the third gene detection field-effect device, and classifying into three patterns; a pattern in which V1 is larger than V2 (V1>V2), a pattern in which V1 and V2 is almost the same (V1≈V2), and a pattern in which V1 is smaller than V2 (V1<V2) and displaying the same; and measuring an output value of the gene detection field-effect device.

2. The method of analyzing gene polymorphism according to claim 1, wherein the nucleic acid probes are immobilized to the respective insulation films of the first and second gene detection field-effect devices, wherein the wild-type nucleic acid probe of the first gene detection field-effect device comprise a base sequence which is complementary with a wild-type base sequence of the target gene, and the mutant-type nucleic acid probe of the second gene detection field-effect device comprise a base sequence which is mutated at a non-immobilized end of the wild-type nucleic acid probe.

3. The method of analyzing gene polymorphism according to claim 1, wherein at least one type of the nucleic acid probe is selected from the group consisting of oligonucleotide, a complementary DNA (cDNA) and peptide nucleic acid (PNA).

4. The method of analyzing gene polymorphism according to claim 1, wherein the nucleic acid probe of the first and second gene detection field-effect devices are immobilized via a metal electrode.

5. The method of analyzing gene polymorphism according to claim 4, wherein at least one type of the metal electrode is selected from the group consisting of white gold, gold, silver, palladium, titan, and chrome.

6. The method of analyzing gene polymorphism according to claim 1, wherein a heater and a temperature sensor are further integrated.

7. The method of analyzing gene polymorphism according to claim 1, wherein the insulation films of the first, second, and third gene detection field-effect devices are formed of silicon nitride.

* * * * *